United States Patent [19]
Brush

[11] 4,150,666
[45] Apr. 24, 1979

[54] TUBE HOLDER FOR BLOOD COLLECTION TUBES OF DIFFERENT SIZES

[75] Inventor: Donald C. Brush, Ballwin, Mo.

[73] Assignee: Sherwood Medical Industries Inc., St. Louis, Mo.

[21] Appl. No.: 810,256

[22] Filed: Jun. 27, 1977

[51] Int. Cl.$^2$ .............................................. A61B 5/00
[52] U.S. Cl. .............................. 128/2 F; 128/DIG. 5
[58] Field of Search ................ 128/2 F, DIG. 5, 276, 128/218 D, 218 DA, 218 R, 220, 221, 215, 216

[56] References Cited

U.S. PATENT DOCUMENTS

| | | | |
|---|---|---|---|
| 1,881,415 | 10/1932 | Tingleff | 128/276 |
| 2,460,641 | 2/1949 | Kleiner | 128/276 |
| 3,115,135 | 12/1963 | Sarnoff | 128/218 DA |
| 3,931,815 | 1/1976 | Takatsuki | 128/2 F |

FOREIGN PATENT DOCUMENTS 829724  3/1960  United Kingdom ................ 128/218 D Primary Examiner—John D. Yasko
Attorney, Agent, or Firm—Stanley N. Garber; William R. O'Meara

[57] ABSTRACT

A blood collection needle and tube holder having a barrel open at one end for receiving a blood collection tube and having an end wall at the opposite end carrying an axially extending double-ended needle cannula. The barrel has longitudinally extending, resilient, interior walls inclined from the open end inwardly toward the longitudinal axis of the barrel whereby tubes of different sizes can be selectively inserted in the holder and guided by the inclined resilient walls. A size range pre-adjustment can be provided to change the angle between the longitudinal axes of the guide arms and the longitudinal axis of the barrel.

12 Claims, 10 Drawing Figures

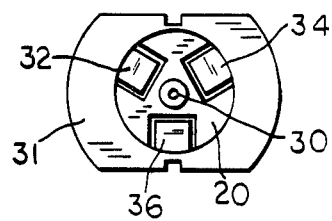
FIG. 2
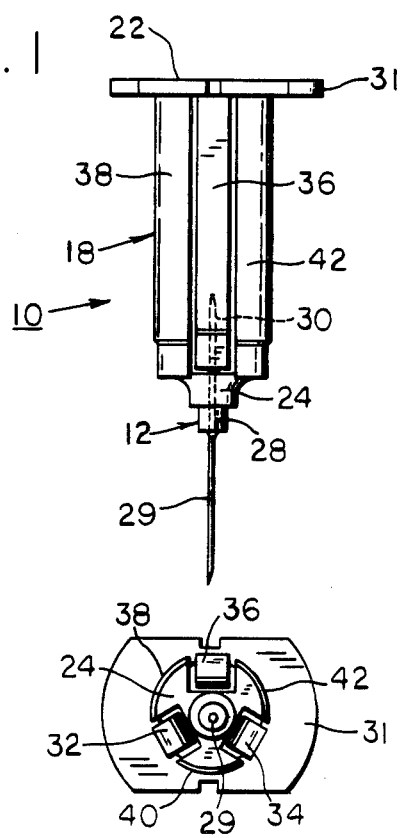
FIG. 1
FIG. 3
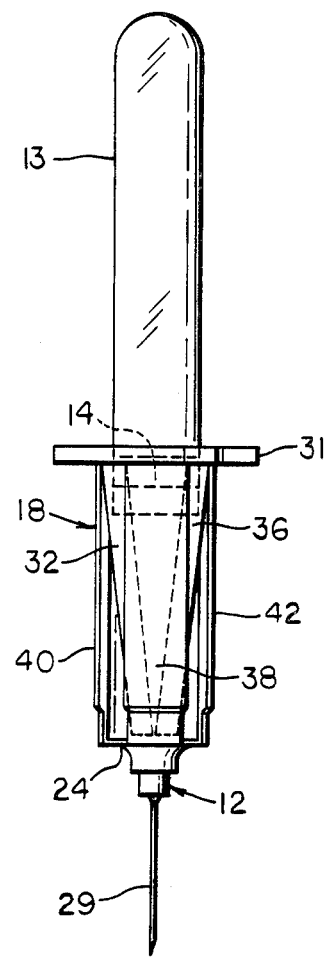
FIG. 4
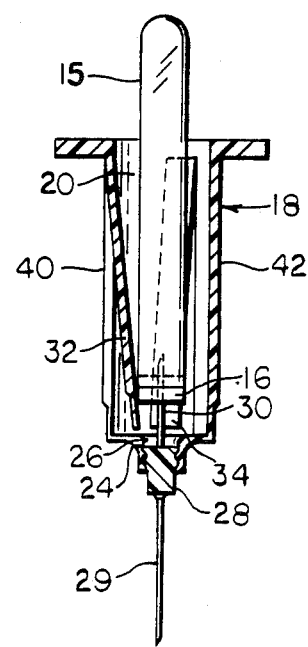
FIG. 5

TUBE HOLDER FOR BLOOD COLLECTION TUBES OF DIFFERENT SIZES

BACKGROUND OF THE INVENTION

This invention relates to tube holders for blood collection tubes and more particularly to a tube holder for use with collection tubes of different sizes.

Tube holders generally include a cylindrical body or barrel open at one end for receiving an evacuated blood collection tube and an end wall at the opposite end for supporting a double-ended needle cannula. The needle has a distal end for insertion into a vessel of a patient and a proximal end within the barrel for penetrating the stopper of the collection tube. The tube is guided by the barrel toward the proximal end of the needle so that the needle properly enters the central portion of the stopper to effect fluid communication with the interior of the tube.

A tube holder of given size will, of course, accommodate and accurately guide a blood collection tube of complementary size. However, since blood collection tubes employed in taking blood samples for various kinds of blood tests vary significantly in size, it is often necessary to employ tube holders of different sizes. Also, it is often desirable to take a number of blood samples for different blood tests from the same patient while maintaining the same tube holder needle in the vein of the patient in order to avoid multiple punctures. Where such collection tubes vary in size, difficulties can occur if an attempt is made to use the same tube holder for all such tubes. For example, it is difficult to maintain the holder steady with the distal portion of the needle in the patient, while attempting to properly seat the stopper of a small tube onto the proximal portion of the needle where the tube holder is of a size capable of use with a relatively large tube.

SUMMARY OF THE INVENTION

Accordingly, it is an object of the present invention to provide a tube holder which is capable of receiving and guiding collection tubes of various sizes and which substantially avoids the above-mentioned disadvantages.

In accordance with one form of the present invention, a tube holder is provided which includes a body open at one end for selectively receiving collection tubes of different sizes, an end wall at the opposite end adapted to receive an axially extending double-ended needle, and resilient inner walls engageable with a collection tube inserted into the open end of the body for guiding the tube toward the needle so that the needle will enter the central portion of the tube stopper.

These as well as other features and advantages of the present invention will be apparent from the following detailed description and accompanying drawings.

BRIEF DESCRIPTION OF THE DRAWINGS

FIG. 1 is a side elevational view of a tube holder in accordance with a preferred embodiment of the invention;

FIG. 2 is a top plan view of the tube holder of FIG. 1;

FIG. 3 is a bottom plan view of the tube holder of FIG. 1;

FIG. 4 is a side elevational view of the tube holder of FIG. 1, slightly rotated, with a relatively large blood collection tube shown entering the holder;

FIG. 5 is a cross-sectional elevational view of the holder of FIG. 1 with a relatively small blood collection tube disposed in the holder;

DESCRIPTION OF THE PREFERRED EMBODIMENTS

Figure 9:
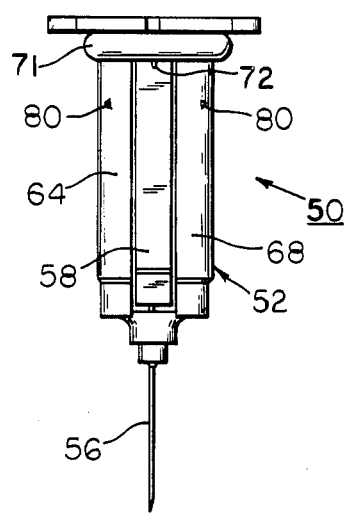
FIG. 9 is a side elevational view of the tube holder of FIG. 6 with the holder pre-adjusted to receive collection tubes of relatively small sizes.

Referring now to the drawings, and particularly to FIGS. 1-5, a needle and tube holder 10 is shown carrying a double-ended needle cannula assembly 12. The holder 10 is adapted for use with evacuated blood collection containers or tubes of various sizes. For example, a relatively large collection tube 13 including a stopper 14 is shown entering the holder 10 in FIG. 4; and a relatively small collection tube 15 having a stopper 16 is shown in the holder 10 in FIG. 5. The stoppers are of a suitable rubber which maintain the negative pressure in the tube and which are self-sealing after needle penetration.

The holder 10 includes a barrel 18 having a chamber 20 with an open proximal end 22 for receiving a collection tube, and a wall 24 at the distal end of the chamber for receiving the needle assembly 12. As seen in FIG. 5, distal end wall 24 has a central or axial hole 26 extending through it and which is provided with threads for threadedly receiving a threaded hub 28 of the needle assembly 12. The needle assembly 12 has an outwardly or distally extending distal needle portion 29 for insertion into a vessel, such as a vein of a patient, and an integral inner needle portion 30 extending along the longitudinal axis and proximally from the end wall 24 of the holder for piercing the stopper of a collection tube and effecting fluid communication between the patient's vessel and the interior of the collection tube. An integral finger flange 31 is provided on the proximal end 22 for facilitating the insertion of a tube in the holder. The same holder may be used with a plurality of different collection tubes, for example, the tubes may contain different chemicals for different blood tests. The tubes may be of different sizes for obtaining samples of different quantities of blood for various tests.

The barrel 18 has resilient chamber walls or elongate guide arms 32, 34 and 36 which extend longitudinally from the proximal end 22 to a point closely adjacent the distal end of the holder or end wall 24. These three resilient guide arms are equally circumferentially spaced from each other and circumferentially alternate with three longitudinally extending arcuate walls 38, 40 and 42 which are fixed, relatively rigid walls connecting the proximal and distal ends of the holder together. The barrel 18 may be molded of relatively rigid plastic, such as polypropylene or the like and in integral form.

The guide arms 32, 34 and 36 are normally similarly inclined from the proximal end toward the longitudinal axis of the holder so that they tend to converge near the distal end of the holder 10. The guide arms are integrally connected to the holder only at their proximal ends and are flexible radially outwardly from the longitudinal axis of the holder when a tube is inserted into the holder. The guide arms or walls 32, 34 and 36 provide a conical-like guide for collection tubes of various sizes or diameters so that the needle 30 will enter and pierce the central portion of the stopper of the inserted collection tube.

In use, a sterile needle assembly 12 may be threaded into the distal end of barrel 18 and then the distal end 29 of the needle inserted into a vessel of the patient, such as a vein. A blood collection tube, for example, the relatively large tube 13 of FIG. 4, is inserted into the open proximal end 22 of the barrel 18 and moved longitudinally toward the distal end wall 24 of the barrel. As the tube 13 is moved in the barrel, the distal end of the tube or stopper 14 engages and slides along the three resilient walls or guide arms 32, 34 and 36 with the walls flexing radially outwardly as the tube moves toward the distal end of the barrel. During this movement, the guide arms apply equal radial forces on the tube so that it tends to be maintained centered along the axis of the barrel or concentric with the barrel. The distal portion 30 of the needle pierces the central or axial portion of the stopper 14 and communicates with the interior of the tube 13. The tube is moved relative to the holder until it engages end wall 24. When the needle 30 pierces the stopper, the vein is in fluid communication with the interior of the tube whereupon the negative pressure therein causes the flow of blood from the vein to the tube. After the tube 13 has been filled with a desired amount of blood, it is move proximally relative to the holder to separate it from the holder. The guide arms 32, 34 and 36 then return to their normal or unstressed condition shown in FIGS. 1–3.

In many cases, more than one blood collection tube will be used to obtain blood samples in this manner and without removing the distal portion 29 of the needle from the patient's vein between samples. The tubes may vary in size depending upon the amount of blood to be drawn and type of tests to be made. Such tubes may contain different test chemicals.

In FIG. 5, the relatively small collection tube 15 is shown disposed in the barrel 18 of holder 10 with the stopper 16 pierced by the proximal needle portion 30 and with the tube almost fully inserted into the holder. As the tube 15 is moved into the holder it engages the three guide arms or walls 32, 34 and 36 which move outwardly while the resiliency of the arms tends to maintain the tube centered concentric with barrel 18 so that the desired central or axial portion of the stopper is pierced by the needle portion 30. Tube 15 is guided in the same manner as tube 13 except that tube 15 is moved further into holder 10 before the flexible guide arms begin to guide it centrally.

The collection tube engages the guide arms as it moves longitudinally through the barrel to progressively urge the three guide arms radially outwardly against the resiliency of the arms. After the tube 15 is filled and removed from the holder, the arms 32, 34 and 36 again return to their normal, unstressed substantially inclined position shown in FIGS. 1–5 because of the inherent resiliency of the arms.

Since holder 10 can be employed with blood collection tubes of substantially different sizes, the needle does not have to be removed and reinserted even though relatively small and large collection tubes are used.

A tube holder 50 of modified construction is shown in FIGS. 6–10 which includes a barrel 52 with a finger flange 53 at the proximal end and a needle assembly 54 threadedly connected to the distal end wall 55 of the barrel. Needle assembly 54 has a double-ended needle 56. The barrel 52 is provided with three resilient, longitudinally extending, flexible guide arms or walls 58, 60 and 62. The guide arms are circumferentially spaced 120° apart and alternate with rigid longitudinally extending fixed side walls 64, 66 and 68. Holder 50 is also provided with a size range pre-adjustment device, indicated generally at 70 and which is discussed hereafter.

Figure 6:
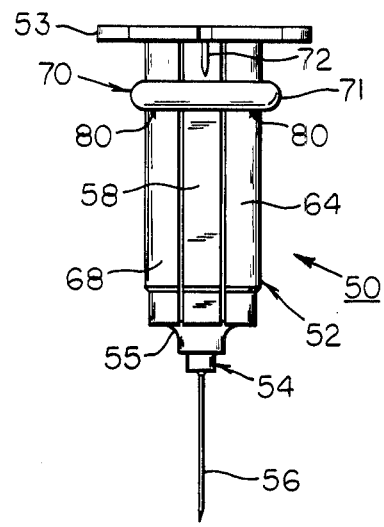
FIG. 6 is a side elevational view of a tube holder in accordance with a modified embodiment of the invention.
Figure 8:
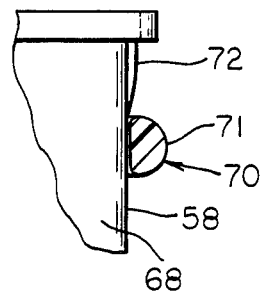
FIG. 8 is a fragmentary side elevational view partly in section of the holder of FIG. 6.
Figure 7:
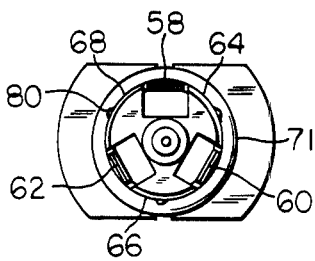
FIG. 7 is a bottom plan view of the tube holder of FIG. 6.

The guide arms 58, 60 and 62 are integrally connected to the proximal end of barrel 52 and are formed so that they are normally (unstressed condition) inclined either slightly radially inwardly toward the distal end and holder axis (but less than the normal incline of the guide arms in the embodiment of FIGS. 1–5) or such that they are parallel to each other with their distal ends spaced a maximum distance apart, the condition shown in FIGS. 6–8.

The size range pre-adjustment device 70 of holder 50 includes an adjustment ring 71 having a fixed inner diameter slightly greater than the outer diameter of the barrel 52. The ring is axially movable between its "large size" position, shown in FIGS. 6–8, to its "small size" position, shown in FIGS. 9 and 10. The ring 71 cooperates with axially extending inclined ramps 72, 74 and 76 integrally formed respectively on the exterior of the guide arms 58, 60 and 62. The ramps are inclined radially downwardly from the underside of the flange 53 to a point distally from the flange. In FIGS. 6–8, the ring 71 is disposed between the distal end of the ramps and three stops or abutments 80 which are disposed respectively on the fixed wall portions 64, 66 and 68. The abutments limit the movement of the ring 71 in the distal direction while the flange 53 limits its movement in the proximal direction.

In use, when blood collection tubes in the relatively large size range are to be used, the ring 71 is positioned below the ramps 72, 74 and 76 as shown in FIGS. 6–8, and this allows the guide arms to be substantially parallel to the holder axis. Under these conditions, a relatively large tube, such as tube 13 in FIG. 4, can be inserted into holder 50 and moved along the barrel 52 toward needle 56 with a small or minimum force being required because the guide arms present little opposition to tube movement since the arms are not deflected or are deflected only a small amount by the tube. Because of the relatively small force required to move the tube, there is less tendency on the part of the person taking the blood sample to inadvertently move the holder while the needle is in the patient's vein.

Figure 10:
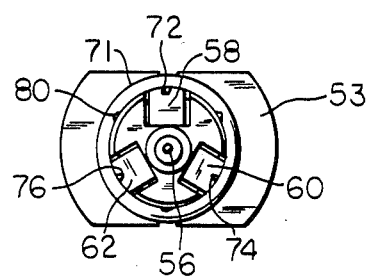
FIG. 10 is a bottom plan view of the tube holder as shown in FIG. 9.

When it is desired to pre-adjust the holder 50 for receiving a collection tube in the relatively small size range, for example, the tube 15 of FIG. 5, the ring 71 is moved axially onto the ramps 72, 74 and 76 as seen in FIGS. 9 and 10. The inner diameter of the ring 71 is less than that of a circle intersecting the outer surfaces of the three ramps so that it causes the guide arms 58, 60 and 62 to become inclined radially inwardly toward the distal end of the holder with their free ends closely spaced near the longitudinal axis of the holder. The ring 71 remains in friction tight relation on the ramps until removed. In this way, a relatively small collection tube will be accurately guided by the guide arms of holder 50 so that the proximal end of needle 56 will enter the central portion of the tube stopper.

Thus, tube holder 50 can be pre-adjusted so that the resilient guide arms have a normally small or zero incline or angle to the longitudinal axis of the holder or a normally large incline to that axis. With this construction, relatively small and large collection tubes are properly guided for movement toward the needle and with the relatively large tubes being moved with relatively little force.

While a two-position size range adjustment is provided by holder 50, the holder could be provided with more than two adjustments, that is, the incline angle of the guide arms could be pre-adjusted to provide more than two normal or pre-adjusted angles. For example, the ring could be moved and frictionally held at a number of different locations on ramps similar to those shown.

Since blood collection tubes of different sizes are readily used with a tube holder of either of the embodiments illustrated herein, the withdrawal of a plurality of blood samples from the same patient without withdrawing or reinserting the needle is readily accomplished with a holder of either of the embodiments illustrated.

In taking multiple samples from the same patient, well-known one-way valves (none shown) have been disposed on the proximal portion of the needle to automatically stop blood flow from the needle each time a collection tube is removed from the holder.

As various changes could be made in the above construction without departing from the scope of the invention, it is intended that all matter contained in the above description and shown in the accompanying drawings shall be interpreted as illustrative and not in a limiting sense.

What is claimed is:

1. A tube holder comprising an elongate body member having a chamber for selectively receiving blood collection containers of different sizes, said body member having means at the distal end thereof for supporting a double-ended needle cannula with the cannula having a distal end portion external to said chamber for insertion into a body vessel and a proximal end portion extending proximally into said chamber for piercing a stopper of a collection container when inserted into said chamber, said chamber having resilient walls extending distally substantially from the proximal end of said chamber to the distal end of said chamber and adapted to be engaged by a collection container for guiding the collection container centrally toward the distal end of said body member such that the proximal portion of the needle enters the central portion of the stopper, and size range adjustment means including means for selectively adjusting the position of said resilient walls with respect to the longitudinal axis of said body member, said size range adjustment means including an inclined ramp on each of said resilient walls adjacent the proximal end thereof, and a slide member of fixed dimension slidable from a first position wherein the distal ends of said resilient walls are relatively far apart to a second position on said ramps to bias the distal ends of said resilient walls closer together.

2. The tube holder of claim 1 wherein said slide member is a ring surrounding said body member.

3. The tube holder of claim 2 further including means on said body member limiting the maximum movement of said slide member.

4. A tube holder comprising an elongate body member having a chamber for selectively receiving blood collection containers of different sizes, said body member having means at the distal end thereof for supporting a double-ended needle cannula with the cannula having a distal end portion external to said chamber for insertion into a body vessel and a proximal end portion extending proximally into said chamber for piercing a stopper of a collection container when inserted into said chamber, said chamber having resilient walls adapted to be engaged by a collection container for guiding the collection container centrally toward the distal end of said body member such that the proximal portion of the needle enters the central portion of the stopper, said resilient walls extending distally substantially from the proximal end of said chamber to the distal end of said chamber and being normally inclined from their proximal ends toward the longitudinal axis of said body member.

5. The tube holder of claim 4 wherein said resilient walls are circumferentially spaced about said body member and connected to said body member at their proximal ends.

6. The tube holder of claim 5 wherein said body member has fixed longitudinally extending portions circumferentially alternating with said resilient walls.

7. The tube holder of claim 6 further including size range adjustment means including means for changing the angle between the longitudinal axes of said resilient walls with respect to the longitudinal axis of said body member.

8. The tube holder of claim 4 wherein said supporting means includes a threaded hole in the distal end of said body member for threadedly receiving a double-ended needle assembly.

9. A tube holder comprising a barrel member of plastic material defining a chamber for selectively receiving and guiding for movement blood collection tubes of different sizes, said chamber being open at the proximal end for receiving a blood collection tube, said barrel member having an end wall at the distal end thereof engageable with a blood collection tube, said end wall including coupling means for connecting a double-ended needle cannula thereto substantially coincident with the longitudinal axis of said barrel and with a portion extending proximally from said end wall, said barrel member having a plurality of circumferentially spaced elongate flexible tube guide arms connected at their proximal ends to the proximal end portion of said barrel member, the longitudinal axis of each of said guide arms when the guide arms are unstressed by a blood collection tube being at an angle to the longitudinal axis of said barrel, said guide arms being resiliently urged radially outwardly upon engagement with a blood collection tube inserted into said barrel to guide the same toward the distal end of said chamber with the collection tube substantially concentric with said barrel whereby the needle portion pierces a central portion of the tube stopper.

10. The tube holder of claim 9 wherein said body member has a radially outwardly extending finger flange at the proximal end of said body member.

11. The tube holder of claim 9 further including tube size range adjustment means on said barrel engageable with said guide arms to move each of said guide arms from a first position wherein the longitudinal axes of said guide arms are in predetermined relationship to the longitudinal axis of said barrel to a second position wherein the longitudinal axes of said guide arms are in a relationship to the longitudinal axis of said barrel that is different from said predetermined relationship.

12. The tube holder of claim 11 wherein each of said guide arms has a ramp descending distally from a proximal location on each guide arm, and a movable ring surrounding said barrel means and having a diameter less than the diameter of a circle intersecting the outer surface of said ramps whereby movement of said ring onto said ramps causes the distal ends of said guide arms to move closer together.

* * * * *

Notice of Adverse Decision in Interference

In Interference No. 100,455, involving Patent No. 4,150,666, D. C. Brush, TUBE HOLDER FOR BLOOD COLLECTION TUBES OF DIFFERENT SIZES, final judgment adverse to the patentee was rendered June 22, 1981, as to claims 4–6 and 8–9.

*[Official Gazette August 25, 1981.]*